United States Patent
Allen et al.

(10) Patent No.: US 11,197,727 B2
(45) Date of Patent: Dec. 14, 2021

(54) ROBOTIC SURGICAL ASSEMBLIES (71) Applicant: Covidien LP, Mansfield, MA (US)

(72) Inventors: Robert Allen, Shelton, CT (US); Chi Min Seow, New Haven, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 15/737,838

(22) PCT Filed: Jun. 22, 2016

(86) PCT No.: PCT/US2016/038656
§ 371 (c)(1),
(2) Date: Dec. 19, 2017

(87) PCT Pub. No.: WO2016/209891
PCT Pub. Date: Dec. 29, 2016

(65) Prior Publication Data
US 2019/0000567 A1 Jan. 3, 2019

Related U.S. Application Data

(60) Provisional application No. 62/183,486, filed on Jun. 23, 2015.

(51) Int. Cl.
*A61B 17/00* (2006.01)
*A61B 34/30* (2016.01)
(Continued)

(52) U.S. Cl.
CPC .............. *A61B 34/30* (2016.02); *A61B 17/00* (2013.01); *A61B 17/29* (2013.01);
(Continued)

(58) Field of Classification Search
None
See application file for complete search history.

(56) References Cited

U.S. PATENT DOCUMENTS 6,113,395 A    9/2000   Hon
6,325,808 B1   12/2001   Bernard et al.
(Continued)

FOREIGN PATENT DOCUMENTS

DE    69322202 T2   7/1999
DE    19842239 A1   3/2000
(Continued)

OTHER PUBLICATIONS

European Patent Office; Search Report in European Patent Application No. 11187650.4 dated Feb. 10, 2012; 6 pages.
(Continued)

*Primary Examiner* — Erica S Lee (57) ABSTRACT

A robotic surgical system includes a surgical robotic arm, an electromechanical instrument, an instrument drive unit, and a coupling shaft. The electromechanical instrument is configured to be detachably coupled to the surgical robotic arm. The electromechanical instrument includes a shaft having a proximal end and a distal end having an end effector. The instrument drive unit includes a motor configured to actuate the end effector. The coupling shaft defines a longitudinal axis and is configured to be coupled between the instrument drive unit and the surgical robotic arm such that the instrument drive unit is rotatable about the longitudinal axis of the coupling shaft relative to the surgical robotic arm or the electromechanical instrument.

13 Claims, 7 Drawing Sheets

(51) Int. Cl.
    *A61B 90/00*        (2016.01)
    *A61B 17/29*        (2006.01)
(52) U.S. Cl.
    CPC ............... *A61B 2017/00022* (2013.01); *A61B 2017/00398* (2013.01); *A61B 2017/00477* (2013.01); *A61B 2034/305* (2016.02); *A61B 2090/034* (2016.02)

(56) References Cited

U.S. PATENT DOCUMENTS

| | | |
|---|---|---|
| 8,828,023 B2 | 9/2014 | Neff et al. |
| 2004/0034282 A1 | 2/2004 | Quaid |
| 2004/0049205 A1 | 3/2004 | Lee et al. |
| 2004/0186347 A1 | 9/2004 | Shose et al. |
| 2006/0244734 A1 | 11/2006 | Hill et al. |
| 2007/0293734 A1 | 12/2007 | Coste-Maniere et al. |
| 2008/0269777 A1 | 10/2008 | Appenrodt et al. |
| 2009/0171184 A1 | 7/2009 | Jenkins et al. |
| 2009/0182226 A1 | 7/2009 | Weitzner et al. |
| 2010/0145521 A1 | 6/2010 | Prisco et al. |
| 2010/0240989 A1 | 9/2010 | Stoianovici et al. |
| 2011/0022229 A1 | 1/2011 | Jang et al. |
| 2011/0118754 A1* | 5/2011 | Dachs, II ............... A61B 34/71 606/130 |
| 2011/0130718 A1 | 6/2011 | Kidd et al. |
| 2012/0045598 A1 | 2/2012 | Hagn |
| 2012/0116416 A1 | 5/2012 | Neff et al. |
| 2016/0106407 A1* | 4/2016 | Lantermann ........... A61B 34/30 606/130 |

FOREIGN PATENT DOCUMENTS

| | | |
|---|---|---|
| DE | 10108547 A1 | 10/2002 |
| DE | 102008064140 A1 | 7/2009 |
| DE | 102013209122 A1 | 11/2014 |
| JP | H09287695 A | 11/1997 |
| JP | H10275006 A1 | 10/1998 |
| JP | 2002537884 A | 11/2002 |
| JP | 2013034859 A | 2/2013 |
| WO | 9901261 A1 | 1/1999 |
| WO | 2009151206 A1 | 12/2009 |
| WO | 2010025943 A1 | 3/2010 |
| WO | 2013018926 A1 | 2/2013 |
| WO | 2014183980 A1 | 11/2014 |
| WO | 2015023834 A1 | 2/2015 |

OTHER PUBLICATIONS

European Search Report corresponding to counterpart European Patent Application No. 16815175.1, dated Jan. 23, 2019; 0.4 dated Feb. 10, 2012; 12 pages.
Japanese Office Action with English translation, dated Apr. 6, 2020, corresponding to counterpart Japanese Application No. 2017-565917; 10 total pages.
Chinese First Office Action dated May 13, 2020 corresponding to counterpart Patent Application CN 201680036276.2.
Chinese Office Action dated Jan. 14, 2021, issued in corresponding Chinese Appln. No. 201680036276, 15 pages.
Indian Office Action dated May 24, 2021, issued in corresponding Indian Appln. No. 201717045717, 7 pages.

* cited by examiner

ROBOTIC SURGICAL ASSEMBLIES

CROSS-REFERENCE TO RELATED APPLICATIONS

The present application is a National Stage Entry of International Patent Application No. PCT/US2016/038656, filed on Jun. 22, 2016, which claims the benefit of and priority to U.S. Provisional Patent Application Ser. No. 62/183,486, filed on Jun. 23, 2015, the entire contents of each of which are incorporated by reference herein.

BACKGROUND

Robotic surgical systems have been used in minimally invasive medical procedures. Some robotic surgical systems included a console supporting a surgical robotic arm and a surgical instrument, having at least one end effector (e.g., forceps or a grasping tool), mounted to the robotic arm. The robotic arm provided mechanical power to the surgical instrument for its operation and movement.

Robotic surgical systems supported many different types of surgical instruments by enabling these instruments to be readily exchanged during a surgical procedure. Typically, this exchange of instruments was performed by detaching the surgical instrument from an instrument drive unit containing motors that actuated the surgical instrument during surgery. This often meant that during the detaching step, a person would have the surgical instrument in one hand and the instrument drive unit in the other hand. In some situations, the instrument drive unit would accidentally drop to the ground either because it had fallen out of the persons hand or because the person had set the instrument drive unit on another object and then it fell to the ground.

There is a need for interchanging surgical instruments with an instrument drive unit while preventing a mishandling of the instrument drive unit during the instrument exchange process.

SUMMARY

In accordance with an aspect of the present disclosure, a robotic surgical system includes a surgical robotic arm, an electromechanical instrument, an instrument drive unit, and a coupling shaft. The electromechanical instrument is configured to be detachably coupled to the surgical robotic arm. The electromechanical instrument includes a shaft having a proximal end and a distal end having an end effector. The instrument drive unit includes a motor configured to actuate the end effector. The coupling shaft defines a longitudinal axis and is configured to be coupled between the instrument drive unit and the surgical robotic arm such that the instrument drive unit is rotatable about the longitudinal axis of the coupling shaft relative to the surgical robotic arm or the electromechanical instrument.

In some embodiments, the instrument drive unit may be rotatable relative to the electromechanical instrument between a first condition and a second condition. In the first condition, a body portion of the instrument drive unit is in alignment with a housing portion of the electromechanical instrument. In the first condition, the body portion of the instrument drive unit may prevent the electromechanical instrument from moving in a proximal direction. In the second condition, the body portion of the instrument drive unit is out of alignment with the housing portion of the electromechanical instrument. In the second condition, the electromechanical instrument may be movable in the proximal direction.

It is contemplated that the system may further include a support structure configured to be coupled to the surgical robotic arm. The support structure may define a passageway and channel therethrough. The passageway is configured for receipt of the electromechanical instrument, and the channel is configured to removably receive the coupling shaft. The support structure may include a button selectively engagable with the coupling shaft to retain the coupling shaft within the channel of the support structure.

It is envisioned that the instrument drive unit may further include a latch configured to be detachably coupled to a housing portion of the electromechanical instrument.

In some aspects, the electromechanical instrument may further include a latch configured to be detachably coupled to the surgical robotic arm.

In some embodiments, the coupling shaft may define a longitudinal channel therethrough configured for receipt of electrical wiring.

It is contemplated that the electromechanical instrument may further include a housing portion having a proximal end and a distal end configured to be coupled to the surgical robotic arm. The shaft of the electromechanical instrument may be supported by the housing portion. The instrument drive unit may further include a body portion defining a central longitudinal axis offset from the longitudinal axis of the coupling shaft. The body portion may have the motor disposed therein and configured to be operably coupled to the proximal end of the housing portion of the electromechanical instrument.

In some embodiments, the robotic surgical system may further include a daisy chain of sensors extending between at least two of the surgical robotic arm, the instrument drive unit, the electromechanical instrument, or the coupling shaft.

In another aspect of the present disclosure, a surgical assembly includes a support structure, an electromechanical instrument, and an instrument drive unit. The support structure is configured to be coupled to a surgical robotic arm. The support structure defines a passageway and a channel therethrough. The electromechanical instrument includes a housing portion and a shaft. The housing portion has a proximal end and a distal end configured to be received within the passageway of the support structure. The shaft has a proximal end supported by the housing portion and a distal end having an end effector. The instrument drive unit includes a body portion and coupling shaft. The body portion defines a central longitudinal axis and has a motor disposed therein. The body portion is configured to be operably coupled to the proximal end of the housing portion of the electromechanical instrument to drive an operation of the end effector of the electromechanical instrument. The coupling shaft of the instrument drive unit extends distally from the body portion and defines a longitudinal axis that is offset from the central longitudinal axis of the body portion. The coupling shaft of the instrument drive unit is configured to be rotatably received within the channel of the support structure such that the body portion of the instrument drive unit is rotatable about the longitudinal axis of the coupling shaft relative to the electromechanical instrument.

It is contemplated that the electromechanical instrument may further include a latch movably attached to the housing portion of the electromechanical instrument. The latch may be configured to be detachably coupled to the support structure.

In some embodiments, the surgical assembly may further include a daisy chain of sensors extending between at least two of the support structure, the instrument drive unit, or the electromechanical instrument. In yet another aspect of the present disclosure, a method of operating a surgical robotic system includes providing a surgical robotic arm, an electromechanical instrument, and an instrument drive unit. The electromechanical instrument includes a housing portion and a shaft. The housing portion has a proximal end and a distal end configured to be coupled to the surgical robotic arm. The shaft has a proximal end supported by the housing portion and a distal end having an end effector. The instrument drive unit includes a body portion and a coupling shaft. The body portion defines a central longitudinal axis and has a motor disposed therein. The body portion is configured to be operably coupled to the proximal end of the housing portion of the electromechanical instrument to drive an operation of the end effector of the electromechanical instrument. The coupling shaft of the instrument drive unit extends distally from the body portion and defines a longitudinal axis that is offset from the central longitudinal axis of the body portion. The coupling shaft of the instrument drive unit is configured to be coupled to the surgical robotic arm. The method further includes rotating the body portion of the instrument drive unit about the longitudinal axis of the coupling shaft relative to the surgical robotic arm and the electromechanical instrument.

In some embodiments, the method may further include operably coupling the distal end of the housing portion of the electromechanical instrument to the surgical robotic arm; and positioning the body portion of the instrument drive unit in abutment with the proximal end of the housing portion of the electromechanical instrument.

It is contemplated that the body portion of the instrument drive unit may be positioned out of alignment with the housing portion of the electromechanical instrument. The electromechanical instrument may be moved in a proximal direction relative to the surgical robotic arm and the instrument drive unit after the body portion of the instrument drive unit is positioned out of alignment with the housing portion of the electromechanical instrument.

The electromechanical instrument may further include a latch movably attached to the housing portion and configured to be detachably coupled to the surgical robotic arm. The method may further include detaching the latch from the surgical robotic arm prior to moving the electromechanical instrument in the proximal direction.

In yet another aspect of the present disclosure, an alternate embodiment of a robotic surgical system is provided. The robotic surgical system includes a surgical robotic arm, an electromechanical instrument, and an instrument drive unit. The electromechanical instrument is configured to be detachably coupled to the surgical robotic arm and includes a shaft having a proximal end and a distal end having an end effector. The instrument drive unit includes a motor configured to actuate the end effector. The instrument drive unit is hingedly coupled to the surgical robotic arm such that the instrument drive unit is pivotable relative to the surgical robotic arm between a first condition and a second condition. In the first condition, the instrument drive unit is in alignment with the electromechanical instrument. In the second condition, the instrument drive unit is out of alignment with the electromechanical instrument.

In some embodiments, the instrument drive unit may further include a body portion and a coupling shaft. The coupling shaft may have a proximal end coupled to the body portion and a distal end hingedly coupled to the surgical robotic arm.

It is contemplated that in the first condition, the body portion of the instrument drive unit may prevent the electromechanical instrument from moving in a proximal direction. In the second condition, the electromechanical instrument may be movable in the proximal direction.

In another aspect of the present disclosure, a sterile interface configured to be coupled to a surgical robotic arm is provided. The sterile interface includes a support structure and a sterile drape coupled to the support structure. The support structure is configured to be coupled to a surgical robotic arm and defines a passageway therethrough configured for receipt of a surgical instrument. The sterile drape houses at least a portion of the support structure therein.

In some embodiments, the support structure may include a main body, a proximal attachment member, and a distal attachment member. The main body may have a proximal end and a distal end and may define the passageway between the proximal end and the distal end. The proximal attachment member may have a rim coupled to the proximal end of the main body and a shaft extending from the rim. The shaft may be disposed within the passageway of the main body. The distal attachment member may be coupled to the distal end of the main body.

It is contemplated that the sterile drape may have a proximal portion captured between the proximal attachment member and the proximal end of the main body, and a distal portion captured between the distal attachment member and the distal end of the main body.

It is envisioned that the sterile drape may be formed from a dielectric material.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical robotic system and surgical assembly thereof including a support structure, an electromechanical instrument, and an instrument drive unit, and methods thereof, are described in detail with reference to the drawings, in which like reference numerals designate identical or corresponding elements in each of the several views. As used herein the term "distal" refers to that portion of the robotic surgical system, surgical assembly, or component thereof, that is further from the user, while the term "proximal" refers to that portion of the robotic surgical system, surgical assembly, or component thereof, that is closer to the user.

As will be described in detail below, provided is a surgical assembly configured to be attached to a surgical robotic arm. The surgical assembly includes an electromechanical instrument configured to be coupled to the surgical robotic arm, and an instrument drive unit for driving an operation of the electromechanical instrument. The instrument drive unit is configured to be rotated out of alignment with the electromechanical instrument such that the electromechanical instrument can be removed from the surgical robotic arm without having to detach the instrument drive unit from the surgical robotic arm.

Figure 1:
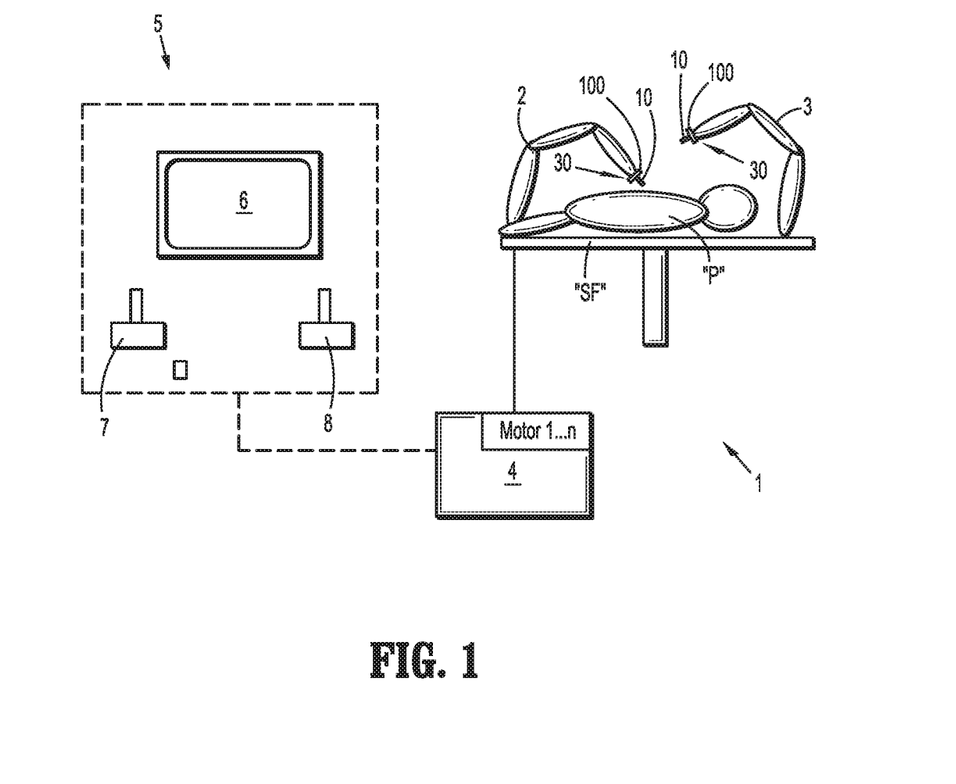
FIG. 1 is a schematic illustration of a robotic surgical system including a surgical assembly in accordance with the present disclosure.
Figure 2:
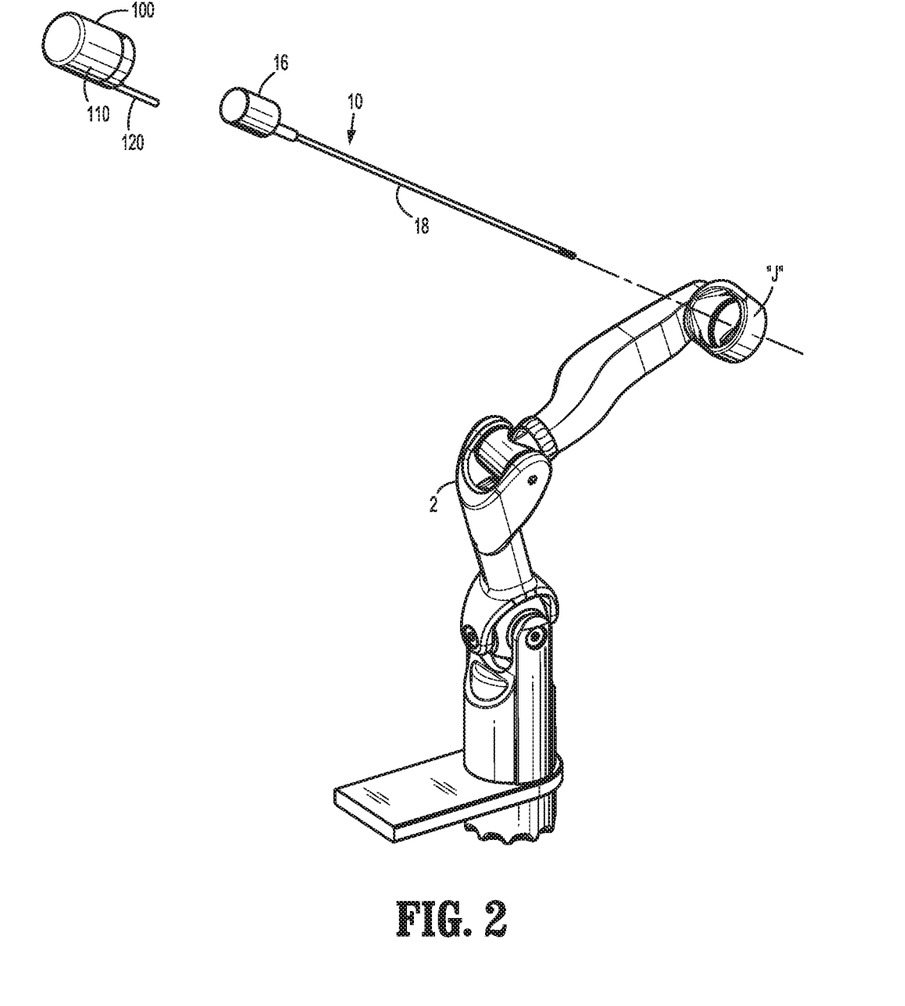
FIG. 2 is a perspective view of a surgical robotic arm of the robotic surgical assembly of FIG. 1 illustrating an electromechanical instrument and an instrument drive unit detached from the surgical robotic arm.

Referring initially to FIGS. 1 and 2, a surgical system, such as, for example, a robotic surgical system 1, generally includes a plurality of surgical robotic arms 2, 3 having an electromechanical instrument 10 and an instrument drive unit 100 removably attached thereto; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 100, and electromechanical instrument 10 (including an electromechanical end effector 12) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 10 (including the electromechanical end effector 12), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of motors M disposed within instrument drive unit 100 that drive various operations of end effector 12 of electromechanical instrument 10. In embodiments, each motor M of instrument drive unit 100 can be configured to actuate a drive rod or a lever arm (not shown) to effect operation and/or movement of electromechanical end effector 12 of electromechanical instrument 10.

For a detailed discussion of the construction and operation of a robotic surgical system, reference may be made to U.S. Patent Application Publication No. 2012/0116416, filed on Nov. 3, 2011, entitled "Medical Workstation," the entire contents of which are incorporated by reference herein.

Figure 3A:
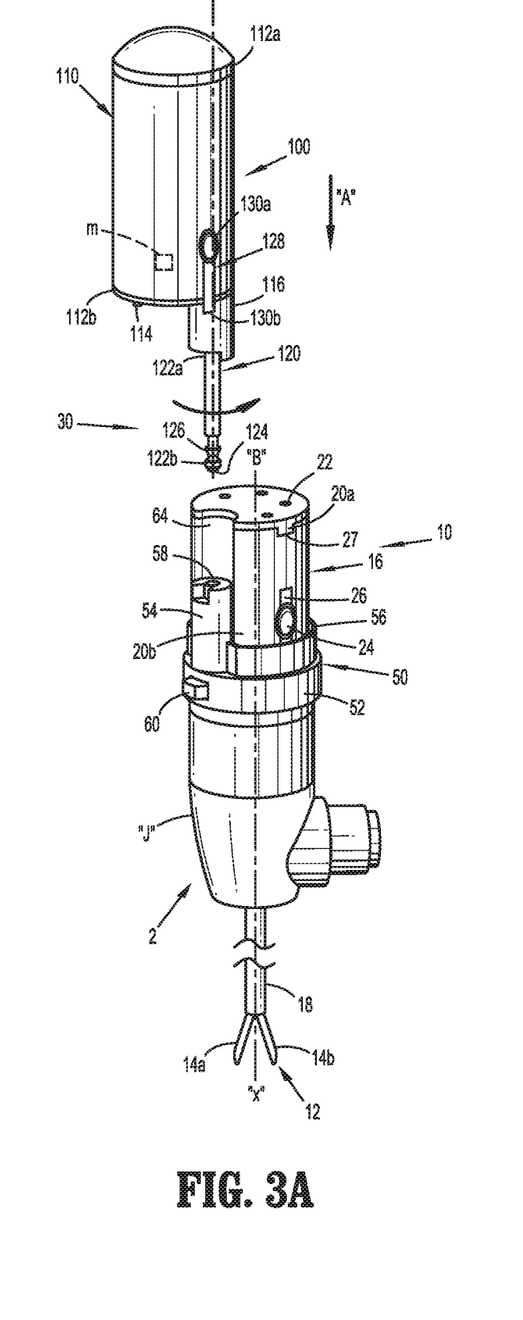
FIG. 3A is a perspective view of the surgical assembly of FIG. 1 with a support structure and the electromechanical instrument of the surgical assembly coupled to the surgical robotic arm, and the instrument drive unit of the surgical assembly separated from the surgical robotic arm.
Figure 3B:
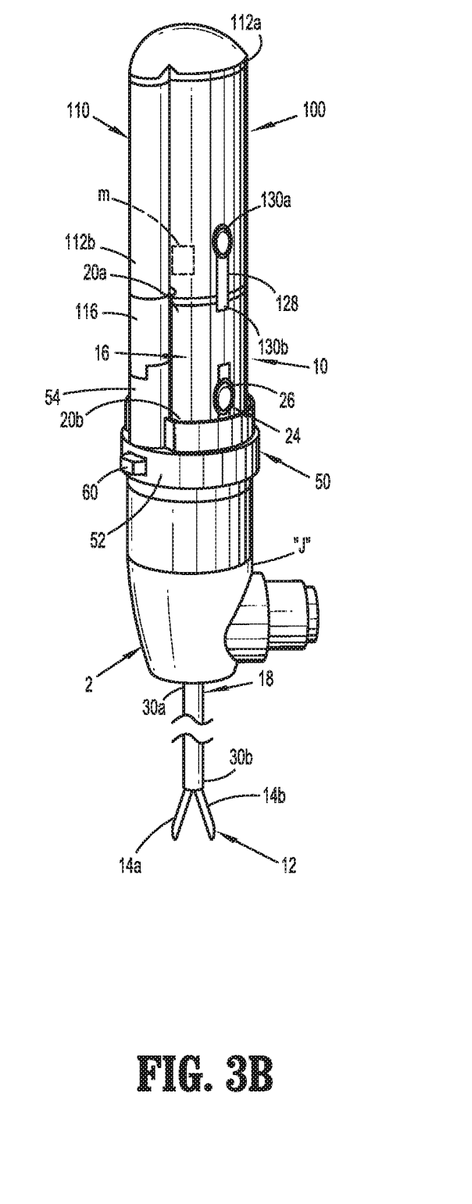
FIG. 3B is a perspective view of the surgical assembly of FIG. 1 in an assembled condition and coupled to a surgical robotic arm.

With reference to FIGS. 2, 3A, and 3B, robotic surgical system 1 includes a surgical assembly 30, which generally includes a support structure 50 configured to be coupled to surgical robotic arm 2, the electromechanical instrument 10 configured to be coupled to support structure 50, and the instrument drive unit 100 configured to be coupled to electromechanical instrument 10. Upon assembly of instrument drive unit 100 with electromechanical instrument 10 (FIG. 3B), instrument drive unit 100 functions to transfer power and actuation forces from motors "M" supported therein to driven members (not shown) of electromechanical instrument 10, to ultimately drive movement of components of end effector 12 of electromechanical instrument 10, for example, a movement of a knife blade (not shown) and/or a closing and opening of jaw members 14a, 14b of end effector 12.

Support structure 50 of surgical assembly 30 is configured to be connected to a joint "J" of surgical robotic arm 2 for coupling electromechanical instrument 10 to surgical robotic arm 2, as will be described in greater detail below. In some embodiments, support structure 50 may be integrally formed with the surgical robotic arm 2. Support structure 50 has an annular member 52 that encloses an upper portion of joint "J" of surgical robotic arm 2, and a cylindrical member or stem 54 extending perpendicularly from a periphery of annular member 52, and which extends parallel to a longitudinal axis "X" of electromechanical instrument 10 when assembled therewith. Annular member 52 of support structure 50 defines a passageway 56 therethrough configured for passage of electromechanical instrument 10. Cylindrical member 54 of support structure 50 is configured for slidable receipt in an arcuate indentation or side channel 64 formed in a housing portion 16 of electromechanical instrument 10. Cylindrical member 54 further defines a longitudinally extending channel or bore 58 therethrough configured for rotatable receipt of a coupling shaft 120 of instrument drive unit 10, as will be described in greater detail below.

Support structure 50 further includes a button 60 movably attached to annular member 52 of support structure 50. Button 60 is selectively movable relative to annular member 52 of support structure 50 between a first, non-depressed condition, in which an internal portion (not shown) of button 60 is disposed within or partially across channel 58 of support structure 50, and a second, depressed condition, in which the internal portion of button 60 does not extend into or partially across channel 58 of support structure 50. Button 60 is configured to selectively engage and lock coupling shaft 120 of instrument drive unit 100 with support structure 50 such that instrument drive unit 100 is prevented from moving along a longitudinal axis "Y" of coupling shaft 120 when coupled to support structure 50, as will be described in greater detail below.

With continued reference to FIGS. 3A and 3B, electromechanical instrument 10 of surgical assembly 30 generally includes a housing portion 16 and a shaft 18 extending distally from housing portion 16. Housing portion 16 has a cylindrical configuration and includes a proximal end 20a and a distal end 20b. A longitudinal axis "X" is defined between proximal and distal ends 20a, 20b. Proximal end 20a of housing portion 16 has a plurality of input drive couplers 22 configured for non-rotatable receipt of a correspondingly shaped output drive coupler 114 extending from each motor "M" of instrument drive unit 100. Housing portion 16 includes driven members (not shown) that extend distally from respective input drive couplers 22. As such, rotation of output drive couplers 114 of instrument drive unit 100, via actuation of respective motors M, rotates respective input drive couplers 22 to effect rotation of respective driven members (not shown) of electromechanical instrument 10.

Distal end 20b of housing portion 16 of electromechanical instrument 10 is configured to be received within passageway 56 of support structure 50 and coupled or keyed to an inner surface (not shown) of support structure 50. In some embodiments, distal end 20b of housing portion 16 may be directly coupled to joint "J" of surgical robotic arm 2 instead of using support structure 50 as a coupler. Electromechanical instrument 10 further includes a latch 24 having a first end 26 pivotably coupled to distal end 20b of housing portion 16 and a second end (not shown). The second end of latch 24 may be configured to be detachably coupled to the interior surface (not shown) of support structure 50 to selectively lock electromechanical instrument 10 with support structure 50. In some embodiments, the second end of latch 24 may be configured to be detachably coupled to joint "J" of surgical robotic arm 2 to selectively lock electromechanical instrument 10 with surgical robotic arm 2 rather than with support structure 50. In some embodiments, housing portion 16 may be attached to support structure 50 and/or surgical robotic arm 2 via various fastening engagements, such as, for example, threaded engagement, clips, friction fit engagement, buttons, a variety of fasteners, and/or a bayonet-type connection. It is further contemplated that instrument 10 may not have latch 24 or any fastening member.

Shaft 18 of electromechanical instrument 10 has a proximal end 30a supported by housing portion 16 and a distal end 30b having end effector 12. The driven members (not shown) of electromechanical instrument 10 extend from housing portion 16 of electromechanical instrument 10 and through shaft 18 of electromechanical instrument 10 to operably couple to various components of end effector 12 such that rotation and/or axial movement of each driven member (not shown) effects actuation of various functions of end effector 12.

End effector 12 generally includes a pair of opposing jaw members 14a, 14b. End effector 12 may be moved, by actuation of the driven members (not shown), from an open configuration wherein tissue (not shown) is received between jaw members 14a, 14b, and a closed configuration, wherein the tissue is clamped and treated. In an embodiment, the opposing jaw members 14a, 14b may be electrically coupled to a cable, and to a generator (not shown), via respective suitable electrical wiring (not shown) extending from instrument drive unit 100 and through shaft 18 of electromechanical instrument 10 to provide an electrical pathway to a pair of electrically conductive, tissue-engaging sealing plates (not shown) disposed on the opposing jaw members 14a, 14b.

In some embodiments, end effector 12 may be in the form of a variety of types of end effectors, such as, for example, disposable loading units, vessel sealing devices, linear stapling devices, circular stapling devices, cutters, graspers, biopsy devices, suturing devices, clip appliers, tack appliers, electrosurgical devices, RF energy devices, cautery devices, harmonic devices, vibratory devices, ultrasonic devices, fastener applicators, etc. In some embodiments, rather than the end effector being a pair of opposing jaw members, the end effector may be an endoscope, an imaging modality, and/or a sensing modality.

With continued reference to FIGS. 3A and 3B, instrument drive unit 100 of surgical assembly 30 includes a body portion 110 and a coupling shaft 120 extending distally from body portion 110. As mentioned above, instrument drive unit 100 has a plurality of motors "M" disposed within body portion 110. Motors "M" function to drive the operations of end effector 12 of electromechanical instrument 10 when instrument drive unit 100 is coupled with electromechanical instrument 10. Body portion 110 has a proximal end 112a and a distal end 112b and defines a central longitudinal axis "X" therebetween.

Distal end 112b of body portion 110 is configured to be operably coupled to proximal end 20a of housing portion 16 of electromechanical instrument 10. Distal end 112b of body portion 110 has a plurality of output drive couplers 114 operably connected to respective motors "M" of instrument drive unit 100. Output drive couplers 114 are configured to be drivingly coupled to input drive couplers 22 of housing portion 16 of electromechanical instrument 10 such that input drive couplers 22 of housing portion 16 of electromechanical instrument 10 are rotated upon independent actuation of motors "M" of instrument drive unit 100.

Body portion 110 of instrument drive unit 100 may have a member 116 extending distally from distal end 112b thereof. The member 116 may be cylindrically shaped or may have any other suitable shape configured to be received within arcuate indentation 64 formed in housing portion 16 of electromechanical instrument 10. Upon assembly or coupling of instrument drive unit 100 with electromechanical instrument 10, a distal end of cylindrical member 116 of instrument drive unit 100 abuts with a proximal end of cylindrical member 54 of support structure 50, as shown in FIG. 3B.

Coupling shaft 120 of instrument drive unit 100 extends distally from distal end 112b of body portion 110 of instrument drive unit 100 and extends or projects through and distally beyond cylindrical member 116 of instrument drive unit 100. Coupling shaft 120 of instrument drive unit 100 has a proximal end 122a and a distal end 122b and defines a longitudinal axis "Y" therebetween. Coupling shaft 120 of instrument drive unit 100 may define a channel 124 extending longitudinally therethrough. Channel 124 may be configured for passage of electrical wiring or optical cabling (not shown) that extends from body portion 110 of instrument drive unit 100 to be connected to electrical components of surgical robotic arm 2.

Proximal end 122a of coupling shaft 120 may extend from distal end 112b of body portion 110 of instrument drive unit 100 such that longitudinal axis "Y" of coupling shaft 120 of instrument drive unit 100 is radially offset from and parallel with central longitudinal axis "X" of body portion 110 of instrument drive unit 100. Distal end 122b of coupling shaft 120 is configured for removable receipt within channel 58 of cylindrical member 54 of support structure 50. Coupling shaft 120 of instrument drive unit 100 and channel 58 of support structure 50 are dimensioned such that upon channel 58 receiving coupling shaft 120 of instrument drive unit 100 therein, coupling shaft 120 of instrument drive unit 100 remains rotatable about longitudinal axis "Y" thereof.

Figure 4A:
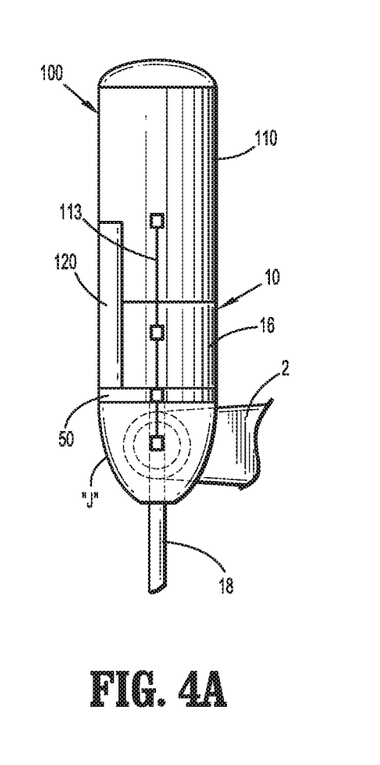
FIG. 4A is a front view of the surgical assembly in an assembled state in which the instrument drive unit and the electromechanical instrument are in alignment and registration with one another and coupled to the surgical robotic arm.
Figure 4B:
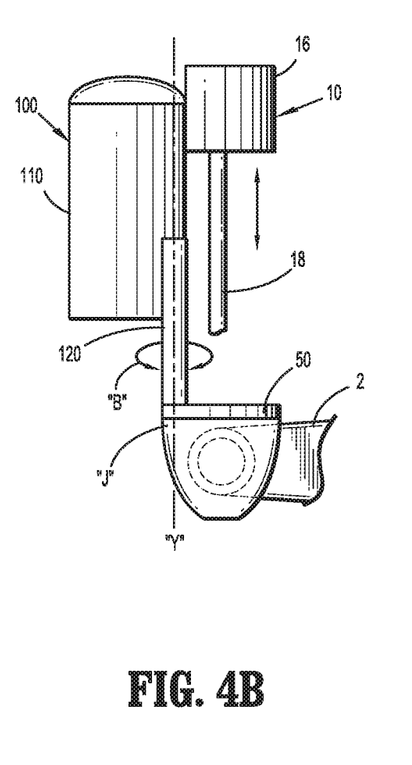
FIG. 4B is a front view of the surgical assembly in a disassembled state in which the electromechanical instrument is detached from the surgical robotic arm and the instrument drive unit is rotated to a position out of alignment and registration with the electromechanical instrument while remaining attached to the surgical robotic arm.

As such, instrument drive unit 100 is rotatable about longitudinal axis "Y" of coupling shaft 120 of instrument drive unit 100, relative to electromechanical instrument 10, between a first condition or position and a second condition or position. In the first condition, body portion 110 of instrument drive unit 100 is in alignment and registration with housing portion 16 of electromechanical instrument 10, as shown in FIGS. 3B and 4A, preventing electromechanical instrument 10 from moving in a proximal direction. In the second condition, as shown in FIG. 4B, body portion 110 of instrument drive unit 100 is out of alignment or registration with housing portion 16 of electromechanical instrument 10 such that electromechanical instrument 10 becomes movable in the proximal direction away from support structure 50 and surgical robotic arm 2 so that electromechanical instrument 10 can be removed from surgical robotic arm 2. It is contemplated that electromechanical instrument 10 may be movable in a proximal direction even when instrument drive unit 100 is in alignment with housing portion 16 of electromechanical instrument 10.

Distal end 122b of coupling shaft 120 of instrument drive unit 100 has an annular cutout 126 formed therein that is configured for removable receipt of a portion of button 60 of support structure 50. As such, upon pressing button 60 of support structure 50, button 60 engages cutout 126 of coupling shaft 120 of instrument drive unit 100 to retain coupling shaft 120 of instrument drive unit 100 in channel 58 of cylindrical member 54 of support structure 50 and prevent coupling shaft 120 from moving along longitudinal axis "Y" thereof in either a proximal or distal direction. In some embodiments, coupling shaft 120 may include a plurality of annular cutouts or notches 126 therealong. Each cutout may be selectively engagable with button 60 of support structure 50. As such, instrument drive unit 120 may be moved between a plurality of vertical positions along longitudinal axis "Y" relative to support structure 50 and surgical robotic arm 2 and be stopped in the selected vertical position.

In one embodiment, surgical assembly 30 may be configured to automatically cam instrument drive unit 100 out of alignment and registration with surgical instrument 10 upon releasing button 60. For example, support structure 50 may include a biasing member (not shown) disposed within channel 58 of cylindrical member 54 of support structure 50 to bias instrument drive unit 100 toward a proximal position by imparting a proximally-oriented force on distal end 122b of coupling shaft 120. Further, a distal end of cylindrical member 116 of instrument drive unit 100 and a proximal end of cylindrical member 54 of support structure 50 may each have a cam feature or annular ramped feature (not explicitly shown) in operative engagement with one another. As such, upon button 60 being disengaged from coupling shaft 120, the biasing member of support structure 50 moves coupling shaft 120 of instrument drive unit 100 proximally relative to support structure 50. As coupling shaft 120 of instrument drive unit 100 moves proximally, the cam features of instrument drive unit 100 and support structure 50 cooperate with one another to rotate instrument drive unit 100 about axis "Y" to position instrument drive unit 120 out of alignment and registration with surgical instrument 10.

In some embodiments distal end 122b of coupling shaft 120 may be fixedly coupled to support structure 50 or surgical robotic arm 2, and proximal end 122a of coupling shaft 120 may be configured to be detachably coupled to distal end 112b of body portion 110 of instrument drive unit 100.

Instrument drive unit 100 further includes a pair of latches 128 disposed on opposite sides of body portion 110 of instrument drive unit 100. Each latch 128 has a first end 130a pivotably coupled to distal end 112b of body portion 110 and a second end 130b. Second end 130b of latch 128 is configured to be detachably coupled to a notch 27 formed in proximal end 20a of housing portion 16 of electromechanical instrument 10 to lock instrument drive unit 100 with electromechanical instrument 10. In some embodiments, body portion 110 of instrument drive unit 100 may be attached to electromechanical instrument 10 via various fastening engagements, such as, for example, threaded engagement, clips, friction fit engagement, buttons, a variety of fasteners, and/or a bayonet-type connection.

In use, with reference to FIGS. 3A, 3B, 4A, and 4B, annular member 52 of support structure 50 is coupled to joint "J" of surgical robotic arm 2. Electromechanical instrument 10 is guided, in a distal direction indicated by arrow "A" in FIG. 3A, through passageway 56 of support structure 50 until latch 24 of electromechanical instrument 10 connects to the interior surface (not shown) of support structure 50 to connect electromechanical instrument 10 to support structure 50.

Next, in one aspect of the present disclosure, body portion 110 of instrument drive unit 100 is aligned with housing portion 16 of electromechanical instrument 10, and coupling shaft 120 of instrument drive unit 100 is aligned with channel 58 of cylindrical member 54 of support structure 50. Instrument drive unit 100 is then coupled to electromechanical instrument 10 by guiding coupling shaft 120 of instrument drive unit 100 into channel 58 of cylindrical member 54 of support structure 50 until cylindrical member 116 of instrument drive unit 100 abuts cylindrical member 54 of support structure 50, and distal end 112b of body portion 110 of instrument drive unit 100 abuts proximal end 20a of housing portion 16 of electromechanical instrument 10, as shown in FIGS. 3B and 4A.

With instrument drive unit 100 coupled to electromechanical instrument 10, output drive couplers 114 of instrument drive unit 100 are drivingly coupled to input drive couplers 22 of electromechanical instrument 10. Distal end 130b of latch 128 of instrument drive unit 100 may be connected to housing portion 16 of electromechanical instrument 10 to detachably lock instrument drive unit 100 with electromechanical instrument 10.

With reference to FIGS. 3A and 4B, to selectively remove electromechanical instrument 10 from support structure 50 and surgical robotic arm 2, without fully disconnecting instrument drive unit 100, instrument drive unit 100 is first rotated about longitudinal axis "Y" of coupling shaft 120, in the direction indicated by arrow "B" in FIGS. 3A and 4B, relative to electromechanical instrument 10 to position body portion 110 of instrument drive unit 100 out of alignment or registration with housing portion 16 of electromechanical instrument 10, as shown in FIGS. 3A and 4B. With body portion 110 of instrument drive unit 100 disposed or rotated out of alignment with housing portion 16 of electromechanical instrument 10, latch 24 of electromechanical instrument 10 may be detached from support structure 50, and electromechanical instrument 10 may be moved in the proximal direction away from surgical robotic arm 2 and support structure 50. As can be appreciated, if instrument drive unit 100 fails to function, instrument drive unit 100 may be moved out of alignment and registration with instrument 10 such that input drive couplers 22 of electromechanical instrument 10 may be accessed manually.

Upon removing electromechanical instrument 10 from surgical robotic arm 2, electromechanical instrument 10 may be sterilized and reused or replaced with another electromechanical instrument. The ability of instrument drive unit 100 to be rotated into and out of alignment or registration with the pathway of electromechanical instrument 10 allows for removal of electromechanical instrument 10 from surgical robotic arm 2 without having to also remove instrument drive unit 100 from surgical robotic arm 2. In this manner, instrument drive unit 100 may remain connected to surgical robotic arm 2 at all times during the surgical procedure.

Further advantages provided by the surgical assemblies described herein may also prevent the instrument drive unit from falling or getting damaged by not requiring that the instrument drive unit be removed to detach the surgical instrument; enable easy removal of the instrument drive unit post-operatively; allow one handed exchange of surgical instruments; improve structural stability and alignment between the instrument drive unit, the electromechanical surgical instrument, and the surgical robotic arm; and minimize the amount of space required to accommodate the instrument drive unit during exchanging surgical instruments.

In some embodiments, the coupling shaft of the instrument drive unit and/or electromechanical instrument 10 may include a means for identifying the unit or instrument, such as: mechanical features, colorimetric markings, optical markings, electrical markings, resistors, reed switches, memory devices, contacts, or other identification technologies. The above features may be configured to actuate or communicate to at least one of: micro-switches, sensors, digital circuits or analog circuits to confirm the status of the instrument drive unit, identify the model and/or serial number of the instrument drive unit or surgical instrument, determine the number of uses of each, determine calibration settings, detect proper loading of the surgical instrument, or determine the load position or the angle/displacement of the coupling shaft of the instrument drive unit.

In one embodiment, as shown in FIG. 4A, surgical assembly 30 includes a daisy chain of sensors 113 extending between instrument drive unit 100, instrument 10, support structure 50, and surgical robotic arm 2. It is contemplated that sensors 113 may extend between any combination of at least two of the above-noted components of surgical assembly 30. Sensors 130 are configured to sense when each of instrument drive unit 100, instrument 10, support structure 50, and surgical robotic arm 2 are properly connected to one another upon assembly.

Figure 5A:
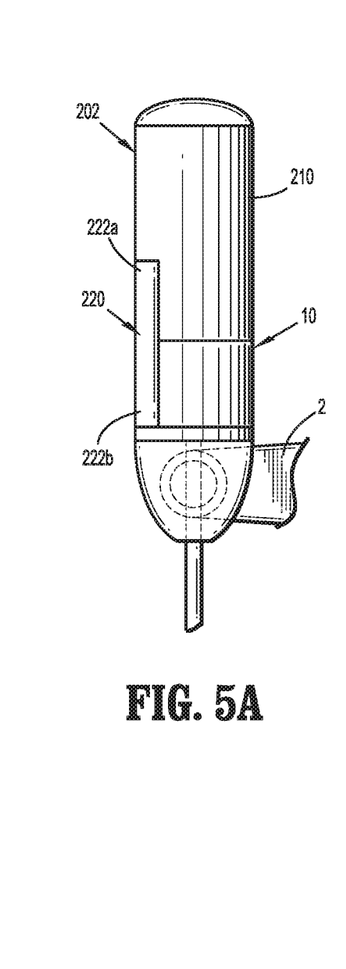
FIG. 5A is a front view of another embodiment of a surgical assembly in an assembled state in which an instrument drive unit and an electromechanical instrument are in alignment and registration with one another and coupled to a surgical robotic arm.
Figure 5B:
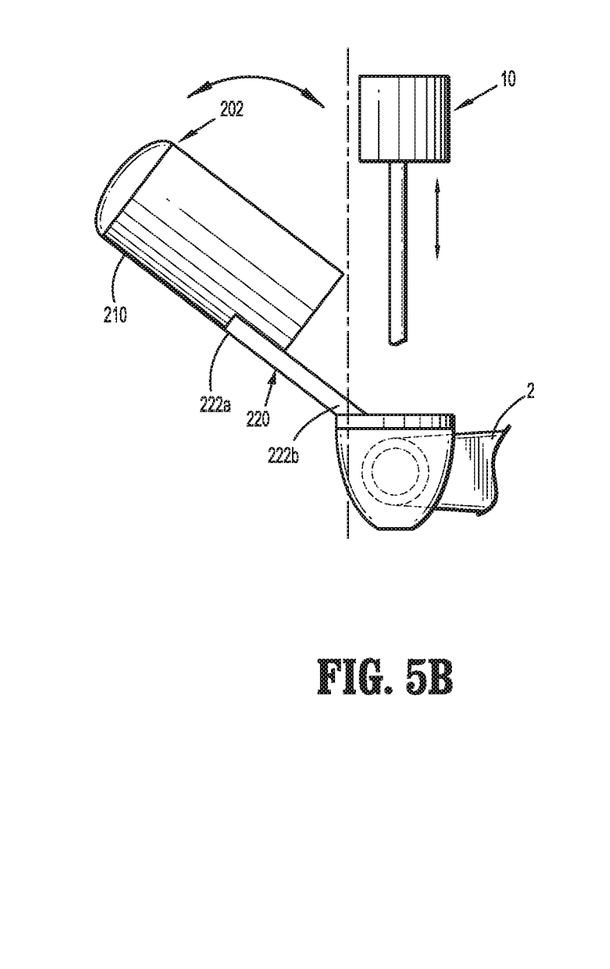
FIG. 5B is a front view of the surgical assembly of FIG. 5A in a disassembled state in which the electromechanical instrument is detached from the surgical robotic arm and the instrument drive unit is pivoted or articulated to a position out of alignment and registration with the electromechanical instrument while remaining attached to the surgical robotic arm.

With reference to FIGS. 5A and 5B, another embodiment of a robotic surgical system is provided and is designated generally by reference numeral 200. Robotic surgical system 200 is similar to system 1 described above, and therefore will only be described with respect to its difference(s). Robotic surgical system 200 differs from system 1 in the manner in which its instrument drive unit 202 is coupled to surgical robotic arm 2, as will be described in detail below.

Instrument drive unit 202 includes a body portion 210 and a coupling shaft 220 extending therefrom. Coupling shaft 220 has a proximal end 222a coupled to body portion 210 and a distal end 222b. Distal end 222b of coupling shaft 220 is hingedly coupled to surgical robotic arm 2 such that instrument drive unit 202 is pivotable or articulatable relative to surgical robotic arm 2 between a first condition, as shown in FIG. 5A, and a second condition, as shown in FIG. 5B. As such, in use, to remove or insert electromechanical instrument 10 to surgical robotic arm 2, instrument drive unit 202 can be pivoted or articulated, about a hinge joint (not explicitly shown), from the first condition, in which instrument drive unit 202 and electromechanical instrument 10 are in alignment and registration with one another, to the second condition, in which instrument drive unit 202 is out of alignment and registration with electromechanical instrument 10. It is contemplated that rather than coupling shaft 50 being hingedly connected to support structure 50 or surgical robotic arm 2, coupling shaft 120 of instrument drive unit 100 instead may include a hinge (not shown) disposed at an intermediate portion of coupling shaft 120 to allow instrument drive unit 100 to bend or articulate thereabout and out of alignment and registration with surgical instrument 10.

Figure 6A:
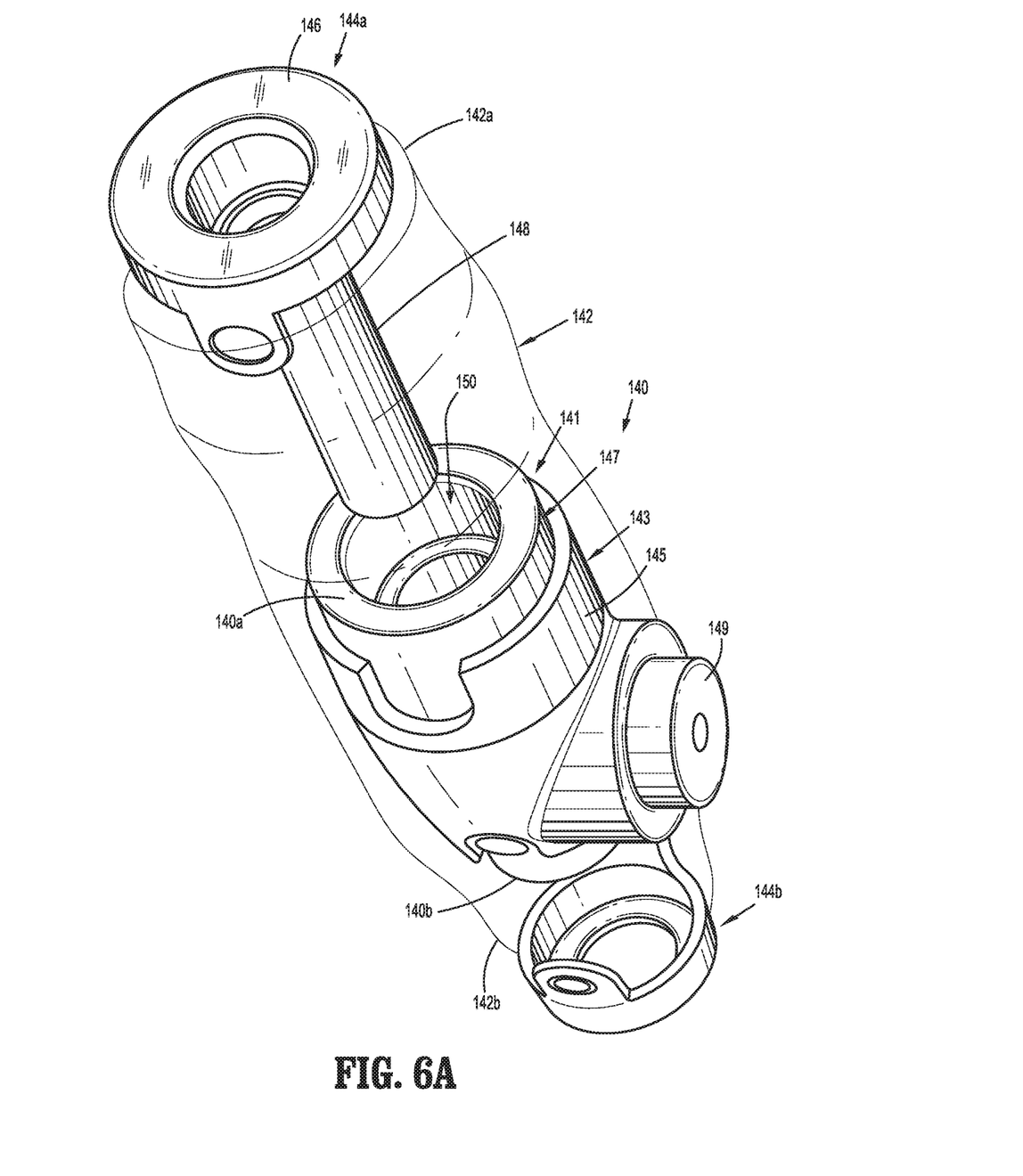
FIG. 6A is a perspective view, with parts separated, of an interface of the surgical robotic arm and attachment members for attachment of a sterile drape.
Figure 6B:
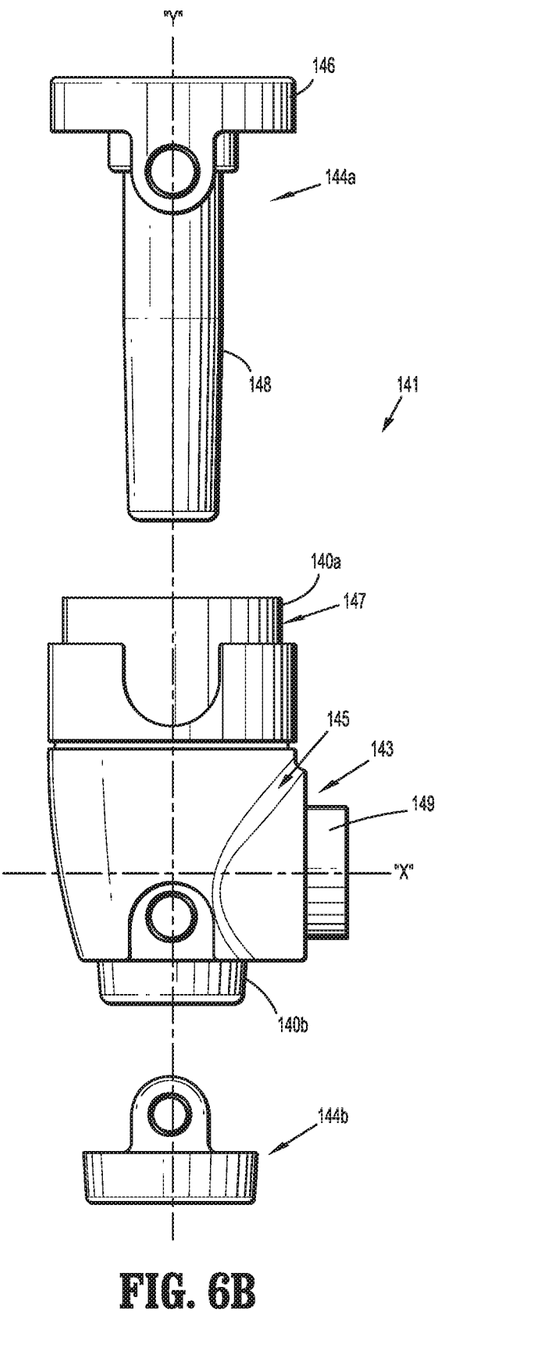
FIG. 6B is a side view, with parts separated, of the interface and attachment members of FIG. 6A.

With reference to FIGS. 6A and 6B, the surgical assemblies of the present disclosure may allow for quick installation of the instrument drive unit 100 to a sterile interface 140 of surgical robotic arm 2 prior to starting a surgical procedure. The sterile interface 140 may replace support structure 50 and be attached to an end of the robotic arm 2 so as to house a surgical instrument, for example, surgical instrument 10. In some embodiments, the sterile interface 140 may enshroud the support structure 50.

Sterile interface 140 includes a support structure 141 and a sterile drape 142 fastened to support structure 141. In some embodiments, sterile drape 142 may be fastened to support structure 141 or be coupled to support structure 141 via a coupling member (not explicitly shown). The coupling member may immovably secure sterile drape 142 to support structure 141. In some embodiments, the coupling member may couple sterile drape 142 to support structure 141 such that components of support structure 141 can be rotated relative to sterile drape 142 about a longitudinal axis "Y" defined by support structure 141 while maintaining the sterile barrier created by sterile drape 142. For example, the coupling member may be an O-ring or an elastomerically sealed surface between sterile drape 142 and support structure 141.

Support structure 141 of sterile interface 140 includes a main body 143, a proximal attachment member 144a, and a distal attachment member 144b. Main body 143 includes an outer body 145 and an inner body 147 rotatably disposed therein. In some embodiments, inner body 147 may be fixedly disposed within outer body 145. Outer body 145 has a mating surface or connector 149 extending laterally therefrom configured to couple to a surgical robotic arm 2. In some embodiments, outer body 145 may be integrally formed with surgical robotic arm 2. Outer and inner bodies 145, 147 of main body 143 are together rotatable about a horizontal axis "X" (FIG. 6B) defined through connector 149. Inner body 147 is rotatable relative to outer body 145 about the longitudinal axis "Y" (FIG. 6B) defined by support structure 141.

Proximal attachment member 144a of support structure 141 has a rim 146 and a cannulated shaft 148 extending therefrom. Rim 146 fits around a correspondingly shaped proximal rim 140a of inner body 147. Cannulated shaft 148 of proximal attachment member 144a is configured for receipt in a passageway 150 defined in main body 143. Instrument 10 (FIG. 2) or any suitable surgical instrument may be passed through cannulated shaft 148 upon assembly. Distal attachment member 144b is configured to be coupled to a distal end 140b of inner member 147. A proximal end 142a of sterile drape 142 is fixed to rim 146 of proximal attachment member 144a and a distal end 142b of sterile drape 142 is fixed to distal end 140b of inner body 147 such that sterile drape 142 enshrouds main body 143 to maintain sterility of sterile interface 140.

In some embodiments, sterile interface 140 may be used to provide electrical isolation or a dielectric barrier for any suitable surgical device (e.g., an electrosurgical or electrocautery device) that is disposed therein and to be coupled to robotic arm 2.

In some embodiments, housing portion 110 of instrument drive unit 100 may be in the form of a clam shell that selectively encloses motors "M" and electronics therein.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A robotic surgical system, comprising:
   a surgical robotic arm;
   an electromechanical instrument configured to be detachably coupled to the surgical robotic arm and including a housing portion, and a shaft having a proximal end coupled to the housing portion, and a distal end having an end effector;
   an instrument drive unit including at least one motor configured to actuate the end effector;
   a coupling shaft defining a longitudinal axis and configured to be coupled between the instrument drive unit and the surgical robotic arm such that at least the instrument drive unit is rotatable about the longitudinal axis of the coupling shaft relative to the electromechanical instrument, wherein when the electromechanical instrument is coupled to the surgical robotic arm, the instrument drive unit is rotatable relative to the electromechanical instrument between a first condition, in which a body portion of the instrument drive unit is in alignment with a housing portion of the electromechanical instrument, and a second condition, in which the body portion of the instrument drive unit is out of alignment with the housing portion of the electromechanical instrument; and
   a support structure configured to be coupled to the surgical robotic arm, the support structure defining:
      a passageway through the support structure and being configured for receipt of the electromechanical instrument; and
      a channel through the support structure, wherein the channel is configured to removably receive the coupling shaft,
   wherein the support structure includes a button selectively engageable with the coupling shaft to retain the coupling shaft of the instrument drive unit within the channel of the support structure.

2. The robotic surgical system according to claim 1, wherein in the first condition, the body portion of the instrument drive unit prevents the electromechanical instrument from moving in a proximal direction, and in the second condition, the electromechanical instrument is movable in the proximal direction.

3. The robotic surgical system according to claim 1, wherein the instrument drive unit further includes a latch movably attached to the instrument drive unit and configured to be detachably coupled to the electromechanical instrument.

4. The robotic surgical system according to claim 1, wherein the electromechanical instrument further includes a latch configured to be detachably coupled to the surgical robotic arm.

5. The robotic surgical system according to claim 1, wherein the coupling shaft defines a longitudinal channel therethrough configured for receipt of electrical wiring.

6. The robotic surgical system according to claim 1, wherein the housing portion has a proximal end, and a distal end configured to be coupled to the surgical robotic arm, the shaft of the electromechanical instrument being supported by the housing portion, wherein the body portion defines a central longitudinal axis offset from the longitudinal axis of the coupling shaft, the body portion having the at least one motor disposed therein and configured to be operably coupled to the proximal end of the housing portion of the electromechanical instrument.

7. The robotic surgical system according to claim 1, further comprising a daisy chain of sensors extending between at least two of the surgical robotic arm, the instrument drive unit, the electromechanical instrument, or the coupling shaft.

8. A surgical assembly, comprising:
   a support structure configured to be coupled to a surgical robotic arm, the support structure defining a passageway and a channel therethrough;
   an electromechanical instrument, including:
      a housing portion having a proximal end and a distal end configured to be received within the passageway of the support structure; and
      a shaft having a proximal end supported by the housing portion and a distal end having an end effector; and
   an instrument drive unit, including:
      a body portion defining a central longitudinal axis and having at least one motor disposed therein, the body portion configured to be operably coupled to the proximal end of the housing portion of the electromechanical instrument to drive an operation of the end effector of the electromechanical instrument; and
      a coupling shaft extending distally from the body portion and defining a longitudinal axis that is offset from the central longitudinal axis of the body portion, the coupling shaft of the instrument drive unit configured to be rotatably received within the channel of the support structure such that at least the body portion of the instrument drive unit is rotatable about the longitudinal axis of the coupling shaft relative to the electromechanical instrument;
   wherein the support structure includes a button selectively engageable with the coupling shaft of the instrument drive unit to retain the coupling shaft of the instrument drive unit within the channel of the support structure.

9. The surgical assembly according to claim 8, wherein the instrument drive unit is rotatable relative to the electromechanical instrument between a first condition, in which the body portion of the instrument drive unit is in alignment with the housing portion of the electromechanical instrument, and a second condition, in which the body portion of the instrument drive unit is out of alignment with the housing portion of the electromechanical instrument.

10. The surgical assembly according to claim 9, wherein in the first condition, the body portion of the instrument drive unit prevents the electromechanical instrument from moving in a proximal direction, and in the second condition, the electromechanical instrument is movable in the proximal direction.

11. The surgical assembly according to claim 8, wherein the instrument drive unit further includes a latch movably attached to the body portion of the instrument drive unit and configured to be detachably coupled to the housing portion of the electromechanical instrument.

12. The surgical assembly according to claim 8, wherein the electromechanical instrument further includes a latch movably attached to the housing portion of the electromechanical instrument and configured to be detachably coupled to the support structure.

13. The surgical assembly according to claim 8, further comprising a daisy chain of sensors extending between at least two of the support structure, the instrument drive unit, or the electromechanical instrument.

* * * * *